United States Patent
Bartig et al.

[11] Patent Number: 6,018,684
[45] Date of Patent: Jan. 25, 2000

[54] SLOTTED PACING/SHOCKING ELECTRODE

[75] Inventors: Jeffrey T. Bartig, Maplewood; Gwen Crevensten, St. Paul, both of Minn.

[73] Assignee: Cardiac Pacemakers, Inc., St. Paul, Minn.

[21] Appl. No.: 09/126,068

[22] Filed: Jul. 30, 1998

[51] Int. Cl.[7] ..................................................... A61N 1/05
[52] U.S. Cl. ........................................... 607/122; 600/374
[58] Field of Search ................... 607/115–117, 119–128, 607/133–138; 606/41; 600/372–381

[56] References Cited

U.S. PATENT DOCUMENTS

| | | |
|---|---|---|
| 4,135,518 | 1/1979 | Dutcher . |
| 4,214,804 | 7/1980 | Little . |
| 4,328,812 | 5/1982 | Ufford et al. . |
| 4,559,951 | 12/1985 | Dahl et al. ............................... 600/374 |
| 4,832,048 | 5/1989 | Cohen ...................................... 607/122 |
| 5,007,435 | 4/1991 | Doan et al. . |
| 5,324,324 | 6/1994 | Vachon et al. ........................... 607/120 |
| 5,330,522 | 7/1994 | Kreyenhagen ........................... 607/122 |
| 5,782,900 | 7/1998 | de la Rama et al. .................... 607/122 |
| 5,935,159 | 8/1999 | Cross, Jr. et al. ....................... 607/116 |

*Primary Examiner*—Jeffrey R. Jastrzab
*Attorney, Agent, or Firm*—Nikolai, Mersereau & Dietz, P.A.

[57] ABSTRACT

A lead for use in conjunction with a cardiac rhythm management device includes an electrode coupled to a conductor. The lead includes an insulative covering in the areas distal and proximal to the electrode. The electrode includes one or more slots bridged by the insulative material to form a more secure joint between the electrode and the insulative material.

7 Claims, 4 Drawing Sheets

SLOTTED PACING/SHOCKING ELECTRODE

BACKGROUND OF THE INVENTION

I. Field of the Invention

This invention relates to leads used in conjunction with cardiac rhythm management devices. More particularly, the present invention relates to the surface electrodes for such leads and a technique for reducing the length of such electrodes while at the same time providing an effective bond between the electrode and adjoining electrically insulative material.

II. Description of the Prior Art

Over the past thirty years, a variety of leads have been developed for use in conjunction with either an implantable heart pacemaker or implantable heart defibrillator. Such leads typically include one or more elongated conductors surrounded by an insulative body, and one or more electrodes coupled to the conductors. The conductors and electrodes provide an electrical path for signals from the heart and delivery of pulses to the heart.

Over the years, a variety of leads have been developed which include one or more ring electrodes. Most often, the ring electrode is a metal band which surrounds the insulative body of the lead. An orifice in the lead body beneath the ring electrode allows the ring electrode to be coupled to a conductor within the lead body.

Recently, "over the wire" leads have been developed.

These leads have been given this name because they are implanted by sliding them over a guidewire. In addition to the conductor, insulative body and electrode, these leads have a central lumen which permits the lead to be passed over the guidewire.

More recently, there has been a need to create leads having smaller cross-sectional diameters. This is true, for example, of leads designed to apply stimulating pulses to the left ventricle without residing in the left ventricle. To be successfully implanted, such leads must pass through the superior vena cava, the right atrium, and the coronary sinus into the great vein of the heart so that the electrode resides in a branch of the coronary vein. This is a tricky path which is best navigated by first using a guidewire and then sliding the lead over the guidewire.

Traditional ring electrodes tend to be relatively long and inflexable. To improve the overall flexability of the lead and thus make it easier to steer, there is a need to reduce the overall length of the electrode. This must be done, however, in a fashion that does not weaken the joints which exists on the proximal and distal ends of the electrode between the edges of the electrode and the electrically insulative body of the lead.

Larger diameter leads have proven to be strong and durable. However, as the diameter is reduced strength can be lost. This is particularly true when ring electrodes are used and joints are formed between the ring electrode and in the insulative body. The joints cause potential weak spots in the lead. Thus, there is a real need to eliminate these weak spots or at least increase the strength of the lead at the interface between the insulative body and the ring electrode. More specifically, there is a real need for a lead having an interface between a ring electrode and insulative body strong enough to handle any axial loading which may be imparted during insertion or removal of the lead.

SUMMARY OF THE INVENTION

The present invention is intended to eliminate potential weak spots at the interface of the insulative body and ring electrode. Specifically, the present invention includes a ring electrode coupled directly to a conductive member in the shape of a coil. The ring electrode includes one or more slots. When the insulative coating (typically silicone) is applied, it is molded over the ring electrode so that it is not only distal and proximal to the ring electrode, but also creates bands of molded silicone across the ring electrode in the slots to provide the required additional axial support. In this arrangement, the ring electrode has exposed surface areas generally flush with the surface of the silicone insulative body. The ring electrode also includes slots filled with silicone bands that were integrally molded with the body portions proximal and distal to the ring electrode.

A greater appreciation of the present invention can be derived from reading the following detailed description of the invention in view of the drawings which form a part of this application.

DETAILED DESCRIPTION OF THE PREFERRED EMODIMENTS

Figure 1:
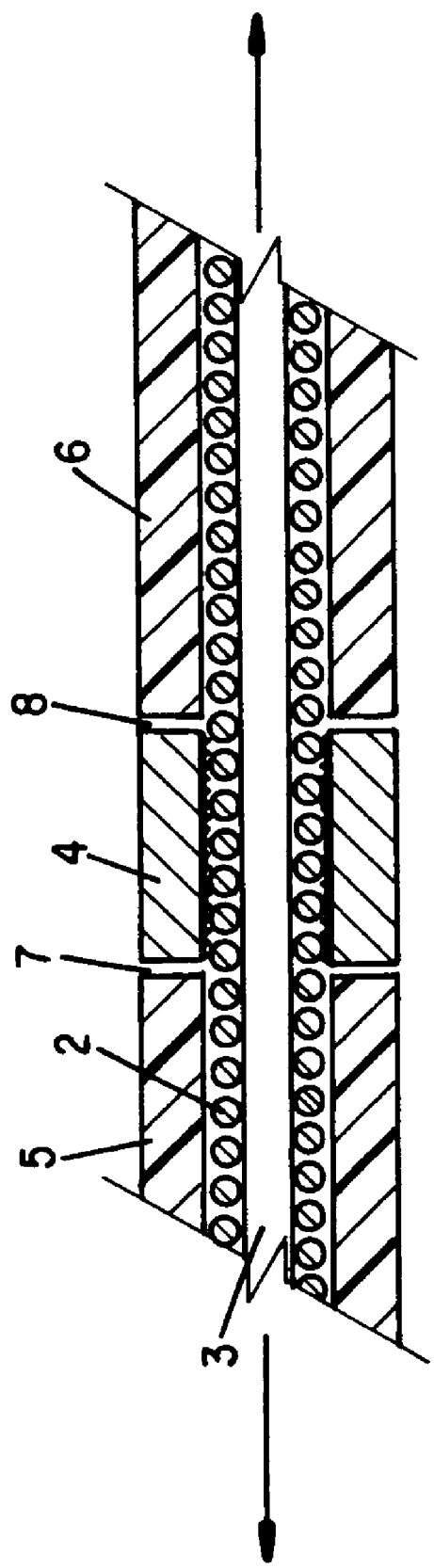
FIG. 1 is a cross-sectional view of a portion of a prior art lead showing the junction between the conductor, a ring electrode and the lead body.

For comparison purposes, a prior art lead 1 is shown in FIG. 1. The prior art lead 1 includes a coil shaped conductor member 2 which surrounds a lumen 3. Also shown is a ring electrode 4. A silicone rubber insulator 5 surrounds the portion conductor member 2 proximal to the ring electrode 4. A second silicone insulator 6 surrounds the portion of conductor 2 distal to the ring electrode 4. FIG. 1 also shows a proximal joint 7 between the ring electrode 4 and the silicone insulator 5 and a distal joint 8 between the ring electrode 4 and the silicone insulator 6. The joints 7 and 8 represent potential weak spots that, when placed under an axial load during insertion of the lead, could render the lead 1 defective. The remaining figures show three embodiments of the present invention designed to strengthen insulator/electrode interface so that it is sufficiently strong to handle normal axial loading.

Figure 2:
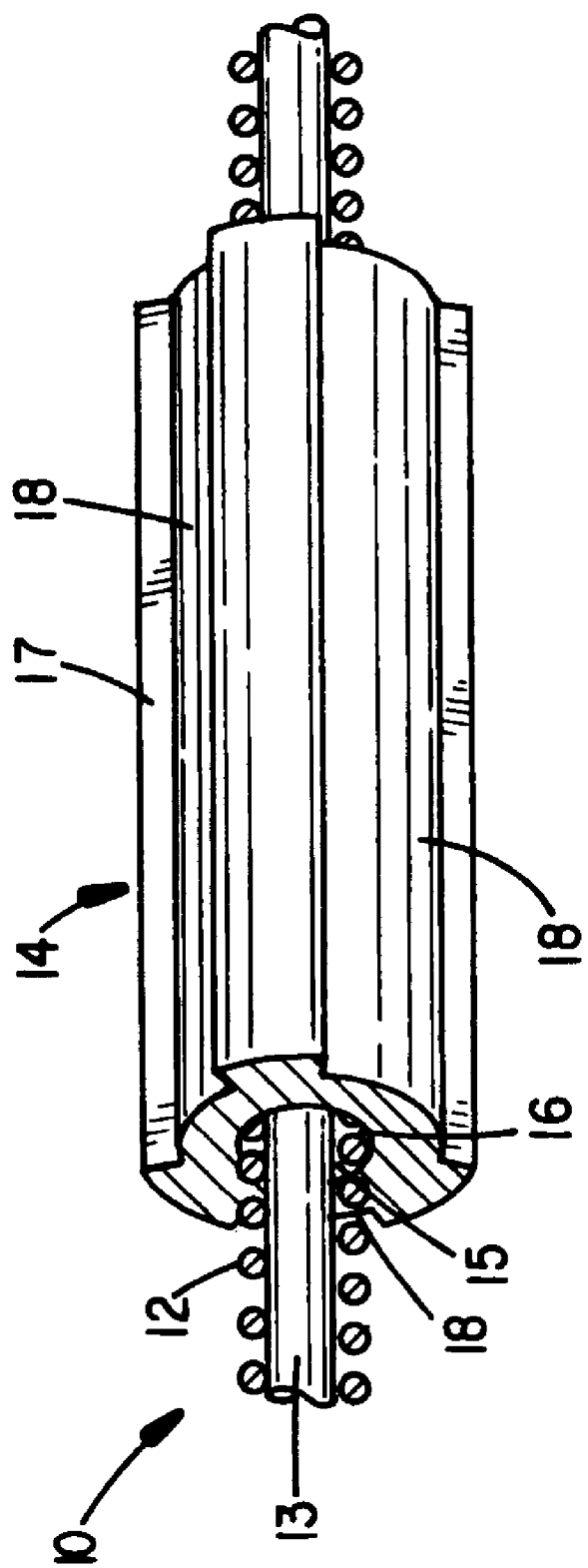
FIG. 2 is a partial perspective view of a lead made in conformance with the present invention showing the interface between a ring electrode and conductor.
Figure 3:
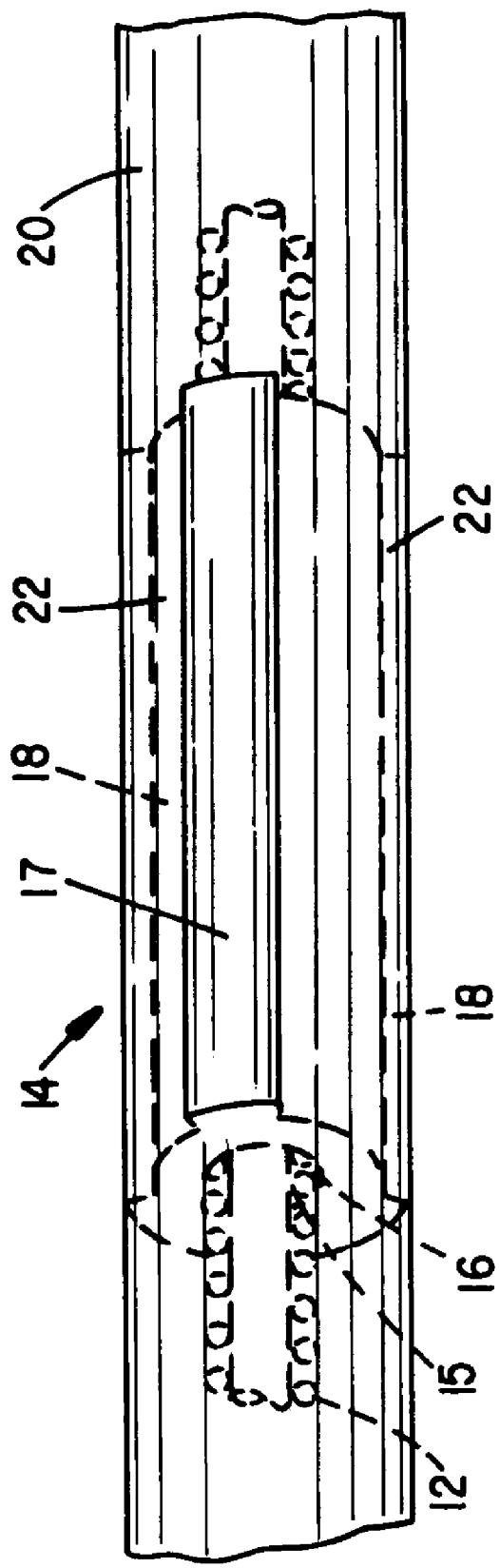
FIG. 3 is a partial perspective view of a lead made in conformance with the present invention showing the interface between the insulation covering and ring electrode with a portion of the ring electrode and the conductor shown in phantom line.
Figure 4:
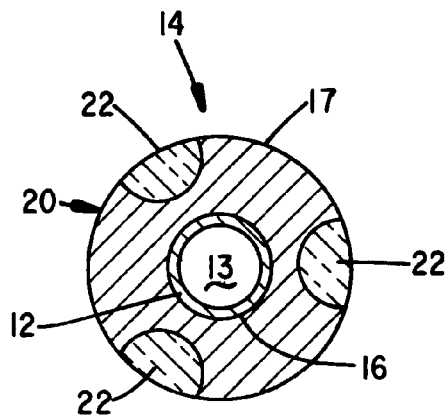
FIG. 4 is a cross-sectional view of a lead made in conformance with the present invention showing the interface between the ring electrode, lead body and conductive member.

As shown in FIGS. 2–4, the lead 10 of the present invention includes a coil-shaped conductor member 12 which surrounds a lumen 13. The ring electrode 14 is coupled to the coil-shaped conductor member 12. This will preferably be accomplished using an axial laser weld between the conductor member 12 and the ring electrode 14.

One important feature of the present invention is the shape of the ring electrode 14. The ring electrode 14 has a generally cylindrical-shaped channel 15 (defined by a wall 16) through its center. During assembly, the coil-shaped conductor member 12 is inserted through the cylindrical-shaped channel 15. An axial laser weld is then used to join the conductor member 12 to the wall 16 of ring electrode 14. The outer surface 17 of the ring electrode 14 is not cylindrical. Instead, it includes one or more slots 18 which extend from one end of the ring electrode 14 to the other. The drawings show three slots 18. However, the number of slots 18 can be as few as one. There is no upper limit to the umber of slots 18. Practically speaking, three to four slots 18 should be adequate.

Once the ring electrode 14 and conductor member 12 have been joined together, an insulative covering 20 can be applied. This coating is typically made of silicone, but other materials having insulative characteristics could also be used. When properly applied, the covering 20 covers both the proximal and distal portions of the conductor and fills the slots 18 to create connecting bridges 22 across the length of the ring electrode 14.

The bridges 22 are integrally formed with the proximal and distal portions of covering 20 and thus serve to strengthen the joints between the ring electrode 14 and covering 20. Of course, the non-slotted portions of the outer surface 17 of the ring electrode 14 remain exposed and uninsulated to provide a current path. To reduce voltage thresholds for the ring electrode 14, the silicone covering 20 could be loaded with a steroid such as, for example, dexamethasone sodium phosphate or dexamethasone acetate. Other suitable steroids may also be used.

Figure 5:
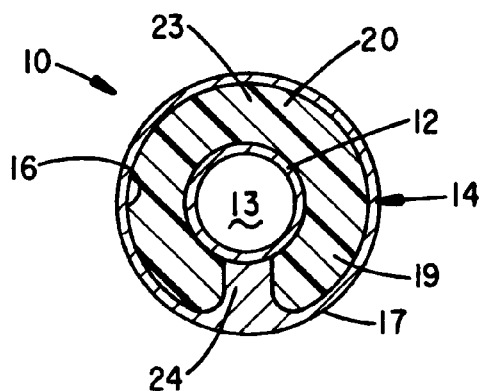
FIG. 5 is a cross-sectional view of a second embodiment in conformance with the present invention.

FIG. 5 is a cross-sectional view of a second embodiment. In this embodiment, the conductor member 12 is surrounded by an insulative covering 20. The insulative covering 20 can be made of silicone rubber or any other suitable material. In this embodiment, the ring electrode 14 has a cylindrical outer surface 17. However, the inner wall 16 is not cylindrically shaped. Instead, one or more teeth 24 are provided. The teeth 24 extend toward the conductor member 12 and are used to weld the conductor member 12 to the ring electrode 14. The teeth are separated by slots 19. These slots 19 extend the length of the ring electrode 14 and are filled to form a bridge 23 integrally formed with and made of the same material as the covering 20. In this embodiment, the bridges 23 cooperate with the teeth 24 and with the remainder of the covering 20 to improve the axial strength of the joints between the covering 20 and ring electrode 14.

Figure 6:
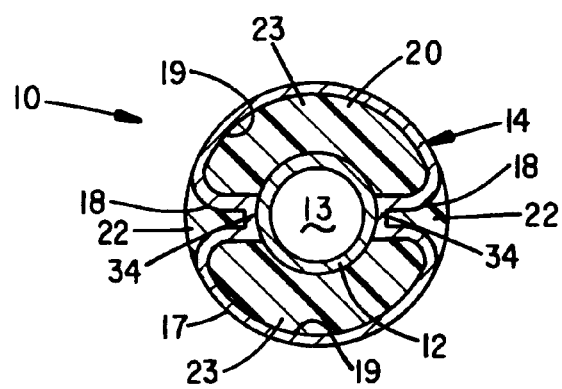
FIG. 6 is a cross-sectional view of a third embodiment made in conformance with the present invention.

FIG. 6 shows a third embodiment. This embodiment again includes a conductive member 12, an insulative covering 20 and a ring electrode 14. In this embodiment, however, neither the wall 16 nor the inner surface 17 are cylindrical. Instead, the wall 16 includes teeth 34 separated by slots 19. The outer surface 17 also includes slots 18 extending into the areas of the ring electrode 14 incorporating the inwardly projecting teeth 34. Thus, when the insulative covering 20 is formed, inner bridges 23 are formed in the slots 19 between the teeth 34 and outer bridges 22 are formed in the slots 18 which extend into the teeth 34. Since the slots 18 and 19 extend the entire length of the ring electrode 14, the bridges 22 and 23 are integrally formed with the portions of the covering 20 proximal and distal to the ring electrode 14.

Electrodes incorporating the features of the present invention have significant advantages over prior art electrodes. First, electrodes made in conformance with the present invention eliminate weak joints between the electrode and the insulative covering. Second, such electrodes accomplish this while minimizing the rigid length of the electrode resulting in greater flexability of the lead design. Thus, leads made in accordance with the present invention are well suited for situations when placement of the electrode requires it to be advanced through the vasculature, such as when the electrode is to be placed in the great vein of the heart in proximity to the left ventricle or in either the right ventricle or right atrium.

What is claimed:

1. A cardiac lead having:

a conductive member;

a ring electrode having an inner center channel defined by a wall and an outer surface, said ring electrode surrounding a portion of and electrically coupled to said conductive member, said ring electrode further having a pair of ends and at least one slot extending across its entire length between such ends;

an insulating member surrounding portions of said conductive member proximal and distal to the ring electrode and having an integrally formed bridge extending across the length of said ring electrode through said slot.

2. The cardiac lead of claim 1 wherein said slot is open to said outer surface.

3. The cardiac lead of claim 1 wherein said slot is open to said inner center channel.

4. The cardiac lead of claim 3 wherein said slot is defined at least in part by a tooth extending toward the center channel.

5. The cardiac lead of claim 4 wherein said ring electrode has a second slot formed in said tooth and open to the outer surface.

6. The cardiac lead of claim 5 wherein said insulating member has a second integrally formed bridge extending across said ring electrode through said second slot.

7. The cardiac lead of claim 1 wherein said ring electrode is welded to said conductive member.

* * * * *